(12) United States Patent
Toussaint

(10) Patent No.: US 11,033,422 B2
(45) Date of Patent: Jun. 15, 2021

(54) TWO-PART MANDIBULAR ADVANCEMENT SPLINT

(71) Applicant: Fahri Yildiz, Cologne (DE)

(72) Inventor: Winfried Toussaint, Heppenheim (DE)

(73) Assignee: Fahri Yildiz, Cologne (DE)

( * ) Notice: Subject to any disclaimer, the term of this patent is extended or adjusted under 35 U.S.C. 154(b) by 715 days.

(21) Appl. No.: 15/542,152

(22) PCT Filed: Jan. 11, 2016

(86) PCT No.: PCT/DE2016/000008
§ 371 (c)(1),
(2) Date: Jul. 7, 2017

(87) PCT Pub. No.: WO2016/112891
PCT Pub. Date: Jul. 21, 2016

(65) Prior Publication Data
US 2018/0263806 A1 Sep. 20, 2018

(30) Foreign Application Priority Data
Jan. 12, 2015 (DE) .................... 20 2015 000 051.7

(51) Int. Cl.
*A61F 5/56* (2006.01)
(52) U.S. Cl.
CPC .................. *A61F 5/566* (2013.01)
(58) Field of Classification Search
CPC ... A61F 5/566; A61F 5/56; A61C 7/00; A61C 7/08; A61C 7/36; A61C 7/0006; A61M 16/0488; A61M 16/049; A63B 71/085

USPC .......................................................... 433/19
See application file for complete search history.

(56) References Cited

U.S. PATENT DOCUMENTS

| | | | | |
|---|---|---|---|---|
| 2,594,832 A | * | 4/1952 | Wentzel ............... | A61C 9/0006 433/41 |
| 3,314,423 A | * | 4/1967 | Boatwright .......... | A63B 71/085 128/861 |
| 4,059,101 A | * | 11/1977 | Richmond ............. | A61H 13/00 601/139 |

(Continued)

FOREIGN PATENT DOCUMENTS

| DE | 29 506 512 U1 | 6/1995 |
|---|---|---|
| DE | 201 02 432 U1 | 4/2001 |

(Continued)

OTHER PUBLICATIONS

International Search Report from the European Patent Office in International Application No. PCT/DE2016/000008 dated Apr. 5, 2016.

(Continued)

*Primary Examiner* — Alireza Nia
*Assistant Examiner* — Kevin S Albers
(74) *Attorney, Agent, or Firm* — The Marbury Law Group, PLLC

(57) ABSTRACT

The invention relates to a prefabricated, two-part mandibular advancement splint for treating snoring and/or obstructive sleep apnea, a telescopically adjustable advancement mount for such a mandibular advancement splint, which is adjustable via a hexagonal nut located in its center, and a ready-to-use kit for producing such a mandibular advancement splint.

20 Claims, 7 Drawing Sheets

(56) References Cited

U.S. PATENT DOCUMENTS

| | | | | |
|---|---|---|---|---|
| 4,382,783 A * | 5/1983 | Rosenberg | ............... | A61C 7/36 |
| | | | | 433/19 |
| 5,462,066 A | 10/1995 | Snyder | | |
| 5,794,627 A | 8/1998 | Frantz et al. | | |
| 5,829,441 A * | 11/1998 | Kidd | ........................ | A61F 5/566 |
| | | | | 128/848 |
| 5,868,138 A | 2/1999 | Halstrom | | |
| 6,012,920 A * | 1/2000 | Woo | ........................ | A61C 7/10 |
| | | | | 433/19 |
| 6,629,841 B1 * | 10/2003 | Skinner | ................ | A61C 9/0006 |
| | | | | 433/43 |
| 7,810,503 B2 * | 10/2010 | Magnin | .................... | A61F 5/566 |
| | | | | 128/848 |
| 7,954,496 B2 * | 6/2011 | Jansheski | ................ | A61F 5/566 |
| | | | | 128/859 |
| 8,360,772 B1 * | 1/2013 | McCarthy | ............ | A61C 9/0006 |
| | | | | 433/41 |
| 2003/0056797 A1 * | 3/2003 | Strong | ..................... | A61F 5/566 |
| | | | | 128/861 |
| 2004/0009451 A1 * | 1/2004 | Skinner | ................. | A61C 9/0006 |
| | | | | 433/43 |
| 2005/0186539 A1 * | 8/2005 | McLean | ............... | A61C 19/063 |
| | | | | 433/215 |
| 2008/0050693 A1 * | 2/2008 | Fischer | ................. | A61C 19/063 |
| | | | | 433/25 |
| 2008/0138766 A1 * | 6/2008 | Jansheski | ................ | A61F 5/566 |
| | | | | 433/140 |
| 2008/0311536 A1 * | 12/2008 | Kim | ..................... | A61C 9/0006 |
| | | | | 433/37 |
| 2011/0195376 A1 * | 8/2011 | Boyd, Sr. | .................. | A61C 7/36 |
| | | | | 433/140 |
| 2011/0247635 A1 * | 10/2011 | Jansheski | ............. | A61C 9/0006 |
| | | | | 128/862 |
| 2012/0041440 A1 * | 2/2012 | Tong | ........................ | A61F 5/566 |
| | | | | 606/60 |
| 2013/0098373 A1 * | 4/2013 | Carlone | .................. | A61F 5/566 |
| | | | | 128/848 |
| 2014/0290668 A1 | 10/2014 | Thornton et al. | | |
| 2014/0332011 A1 * | 11/2014 | Turek | ...................... | A61F 5/566 |
| | | | | 128/848 |
| 2014/0349243 A1 | 11/2014 | Metz | | |
| 2016/0120690 A1 * | 5/2016 | Boyd | ........................ | A61F 5/566 |
| | | | | 128/848 |
| 2017/0296306 A1 * | 10/2017 | Edgren | .................... | A61C 7/22 |
| 2018/0193182 A1 * | 7/2018 | Wiffen | .................... | A61F 5/566 |
| 2018/0325721 A1 * | 11/2018 | Magnin | ................... | A61F 5/566 |
| 2019/0046301 A1 * | 2/2019 | Lovat | .................. | A61C 9/0006 |
| 2019/0336252 A1 * | 11/2019 | Marghalani | .......... | A61C 9/0006 |

FOREIGN PATENT DOCUMENTS

| | | |
|---|---|---|
| DE | 20 2008 011 841 U1 | 12/2008 |
| DE | 10 2009 048 376 B3 | 12/2010 |
| EP | 1 203 570 A2 | 5/2002 |
| EP | 1 516 604 A1 | 3/2005 |
| WO | 2006/136684 A1 | 12/2006 |
| WO | 2010/025700 A1 | 3/2010 |
| WO | 2011/017813 A1 | 2/2011 |
| WO | 2011/127893 A1 | 10/2011 |
| WO | 2012/038663 A1 | 3/2012 |
| WO | 2014/016495 A1 | 1/2014 |

OTHER PUBLICATIONS

International Preliminary Report on Patentability received from the International Bureau of WIPO in Application No. PCT/DE2016/000008 dated Jul. 27, 2017.

* cited by examiner

TWO-PART MANDIBULAR ADVANCEMENT SPLINT

PRIORITY APPLICATION

This application is the U.S. national phase entry under 35 U.S.C. § 371 of PCT Application No. PCT/DE2016/000008, filed Jan. 11, 2016 which claims the priority benefit of German Patent Application No. DE 20 2015 000 051.7 filed Jan. 12, 2015. PCT Application No. PCT/DE2016/000008 is incorporated herein by reference in its entirety. The complete disclosure of the utility patent forming the basis for this, DE 20 2015 000 051.7 dated 12 Jan. 2015, the priority of which is claimed herein, is incorporated by reference here.

BACKGROUND OF THE INVENTION

1. Technical Field

The invention relates to a prefabricated, two-part mandibular advancement splint for treating snoring and/or obstructive sleep apnea.

2. Prior Art

Snoring can be a symptom of the obstructive sleep apnea syndrome, characterized by numerous and repeated nocturnal respiratory arrests, which can result in serious health complications, for example hypertension, cardiovascular diseases, strokes, etc. U.S. Pat. No. 5,462,066 and European patent application EP 1 203 570 have disclosed retainer-like occlusal splints for preventing snoring, serving to advance the mandible slightly forward, since the airways can be opened further in this position, allowing the patient to breathe more freely without snoring.

The known occlusal splints in the form of a one-piece, retainer-like mouthpiece consist of thermoplastic materials with two bite grooves that become deformable when warmed. The patient places the warmed, not yet fitted mouthpiece in the mouth, then presses the teeth of the upper and lower jaw into the moldable plastic of the bite grooves and fit it by biding down on the bite plates of the bite grooves. During this process the plastic cools and regains its solid elasticity, the mouthpiece now being adapted to the patient. During the fitting process it is necessary to make sure to slide the lower jaw forward somewhat to permanently set in an advancement (protrusion). The known occlusal splints have the drawback that an advancement, once set, can only be adapted to the patient's changing needs with difficulty, so that the effect initially achieved worsens over time.

In addition, U.S. Pat. No. 5,868,138 suggests a dental device for treating snoring and obstructive sleep apnea having a maxillary part, a mandibular part, and a connector, wherein the connector retains the lower part in an advanced projecting position relative to the upper part.

German utility patent DE 29 506 512 suggests an anti-snoring device to be worn orally, consisting of an upper and a lower splint, wherein the two splints are provided with a flexible traction, not permitting elongation in the longitudinal direction, which brings the lower jaw into an anterior position when it is lowered.

The splint from German patent application DE 10 2009 048 376 is an individually made splint, which is fixed only in the area of the molars.

German Patent Application DE 201 02 432 suggests an individually fabricated splint that is fixed over the full dentition and has telescopic connectors, wherein the metal parts thereof are provided with a hypoallergenic coating.

The base splint of the US patent application US 2003/0056797 is also individually fabricated and has a frame embedded in this base splint, to which the connector is fastened.

European patent application EP 1 516 604 suggests an intraoral treatment device in which the connectors are arranged intra-occlusal. There is no evidence that the splint is to be discontinuous in the area of the front teeth.

International patent application 2006/136 684 describes a two-part device in which the mandibular splint completely covers the teeth of the lower jaw, but the maxillary splint is formed from 2 partial splints for the molars, the two being connected over an arch (9, 10) in the posterior and anterior regions.

International patent application WO 2011/017 813 likewise suggests an individually shaped device in which 4 partial splints are fixed to the respective molars and the advancement is forced with an elastic band on the side.

The above-named individually fabricated splints must be prepared individually in the dental laboratory after impressions of the maxillary and mandibular splints have been taken.

International patent application WO 2010/025700, on the other hand, suggests a prefabricated, two-part mandibular advancement splint, in which a thermoplastic filling material is located in both a maxillary and a mandibular tray, and these are connected together by way of two rigid advancement mounts. A corresponding mandibular advancement splint with telescopic-type advancement mounts is described in international patent application WO 2011/127893.

In international patent application WO 2012/038 663, a splint based on WO 2010/025700 with a modified design of the advancement knob is suggested.

International patent application WO 2014/016495 A1 on the other hand suggests a similar advancement splint, but here the advancement mounts on the rear side are attached to the maxillary tray via an open ring.

In the international patent applications relating to prefabricated advancement splints, there are no suggestions for omitting the interior wall of the tray in the area of the front teeth.

Such prefabricated, two-part protrusion splints are already being successfully used by many patients in daily practice, e.g., as SomnoGuard® SP. However, many users still experience these as unpleasantly clumsy to use compared to the advancement splints produced individually in the dental laboratory.

Therefore, the goal of the present invention is to supply such patients, who suffer from snoring and/or obstructive sleep apnea, and have compliance problems with the previously known prefabricated splints, with a more sophisticated mandibular advancement splint which differs only marginally in terms of functionality and comfort in use from the many-fold more expensive advancement splints produced individually by the dentist in the dental laboratory after taking a dental impression and remains usable over a long time period.

Surprisingly it has been possible to achieve this goal according to the invention by avoiding the use of rigid walls on the inside of the tray, in the area from the front teeth to the canine teeth.

Despite this feature, the mandibular advancement splints have a long useful life and are easy to manage. In addition, the splints according to the invention can be fitted by the patients themselves without problems, which results in considerable facilitation and cost reduction. Furthermore, the mandibular advancement of the mandibular advancement splints can be easily adapted to the patient's needs.

BRIEF SUMMARY OF THE INVENTION

Thus, the subject matter of the invention is a universally usable two-part mandibular advancement splint for preventing snoring and/or obstructive sleep apnea, comprising a lower and an upper part consisting of an arcuate molding tray, opened respectively during use toward the mandible and maxilla, with a base, an exterior wall and an interior wall, wherein its outer walls on both outsides in the area from the molars to the canine teeth have one or more fixation knobs for fastening an advancement mount, which is fastened rotatably respectively to one fixation knob each of the mandibular and maxillary tray, and brings the mandible into a posterior or anterior position, and these trays respectively contain a thermoplastic filling material that can be shaped to the teeth of the maxilla and mandible, wherein the inner wall of both trays is interrupted in the area of the front to canine teeth.

Preferably, the inner wall of the two trays is completely interrupted in the area of the front to canine teeth and is reduced to a minimal wall edging.

By the use of several rigid advancement mounts of different lengths or telescoping adjustable advancement mounts, the advancement of the maxilla can be easily adapted to the needs of the respective user.

The mandibular advancement splint avoids the time-consuming and expensive individual fabrication in the dental laboratory following previous taking of a dental impression by a dentist or orthodontist. In addition, this universal splint can be adjusted without problems by any doctor—not only a dentist—or even by the patient him/herself, resulting in a considerable simplification in handling.

The invention also concerns a method for making a mandibular advancement splint according to the invention comprising the following steps:
 (a) Forming the molding trays with preformed fixation knobs on the outsides in each case by injection molding;
 (b) Shaping the thermoplastic filling material and fastening it to the trays;
 (c) Producing the advancement mounts;
 (d) Connecting the advancement mounts to the preformed fixation knobs.

An additional object of the invention is a ready-to-use set for making a mandibular advancement splint according to the invention for preventing snoring and/or (obstructive) sleep apnea consisting of
 (A) A lower and an upper part, consisting of an arcuate molding tray opened respectively during use toward the mandible and maxilla, with a base, an exterior wall and an interior wall, wherein its outer walls on both outsides in the area from the molars to the canine teeth have one or more fixation knobs for fastening a telescopically adjustable and/or extendable advancement mounts, and each of these trays contains a thermoplastic filling material that can be shaped to the teeth of the maxilla and mandible, wherein the tray has no inner wall in the area of the front to canine teeth,
 (B) Two or more rigid, telescopically adjustable and/or extendable advancement mounts, and
 (C) Optionally, user instructions for using the mandibular protrusion splint.

The mandibular protrusion splint according to the invention has the advantage that it sits on or adheres firmly to both jaws, comparable to a dental splint, because due to the material composition of the thermoplastic splint filling, a very deep and uniform impression of all teeth is achieved.

In addition, the mandibular advancement splint has the advantage that it can be adapted by any physician or by the patient him/herself within a few minutes, without complications and without special aids. For this reason also a universal standard splint is suitable for almost all jaw shapes. In addition, in a highly advantageous manner, individual adjustment of the mandibular advancement is possible by the use of advancement mounts of different lengths or of telescopically adjustable advancement mounts. The special design of the splint achieves that it is very delicate, and after adjustment of the distance between the upper and lower front teeth, at less than 3 mm, it is very small, which has a highly positive effect on the comfort and acceptance of wearing, and also for the splint to be suitable simultaneously for jaw shapes of different sizes.

BRIEF DESCRIPTION OF THE FIGURES

FIG. 12 shows a schematic representation in top view of the advancement mount in extended (A) and collapsed form (B).

DETAILED DESCRIPTION OF THE INVENTION

Figure 1:
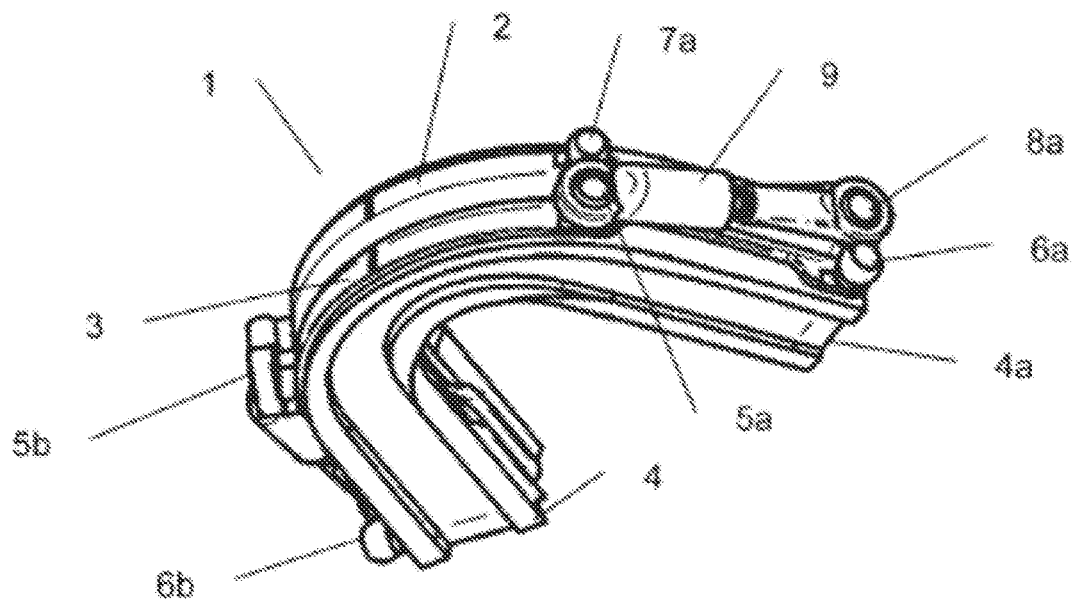
FIG. 1 shows a perspective view obliquely from the bottom and forward of an embodiment of the advancement splint according to the invention.

The advancement splint according to the invention can be universally mass-produced from known materials, for example by injection molding.

Suitable, rigid advancement mounts are described, for example, in WO 2010/025700. Telescoping and optionally extendable advancement mounts can be produced by fabricating the respective telescopic sleeves, provided with fastening elements, by injection molding and connecting them using a connecting element.

Preferably, the rigid advancement mounts and the telescopic sleeves provided with fastening elements are made of polyoxymethylene (POM). Stainless steel, especially V4A stainless steel, is suitable for producing the connecting elements.

The term "advancement splint" or "mandibular advancement splint," as used above and in the following, designates a dental device making it possible to move the lower jaw into a slightly more forward position relative to the upper jaw and thus enlarge the cross section of the upper airways. This results in reduction of snoring and of suspension of breathing due to obstructive sleep apnea.

The term "prefabricated" as is used above and in the following with regard to the mandibular advancement splint designates a mandibular advancement splint which, in contrast to the splints produced individually by the dentist by taking an impression of the user's jaw, is produced on an industrial scale, independently of the individual sizes or shapes of the jaws of the subsequent users. The later adaptation to the shape or size of the jaw is accomplished by having the user bite into the heated and thus soft thermoplastic material, followed by cooling and setting of this material.

The term "thermoplastic filling material" as used above and in the following designates a material that can undergo plastic deformation in the presence of heat, preferably below 70° C., particularly between 40 and 65° C. and adapts closely to a predetermined shape and then retains this said shape on cooling. Suitable materials, among others, are for example polymers and copolymers or mixtures thereof from the group of polyethylenes (PE), polyvinyl acetates (PVA), acrylates and methacrylates, preferably copolymers of PE and PVA, for example those available under the trade name of Elvax® from DuPont. Preferred PE-PVA copolymers are those with PVA contents of 20 to 40, especially 25 to 35%, and polycaprolactone.

Particularly preferred is polycaprolactone, which cures during the cooling process after fitting the tray and surrounds the teeth in a thin, solid layer. Appropriate polycaprolactones are available, for example, under the trade name of Pearlbond® from Lubrizol Advanced Materials Manufacturing Spain, S.L., Gran Vial no. 17, Montmelo 08160 Barcelona or CAPA® 6500 or CAPA® 6800 from Perstorp UK Limited, Baronet Rd., Warrington Wash.4 6HA, UK.

In addition, since polycaprolactone shrinks by about one percent upon cooling and cools firmly, preferred retention (adhesion to the teeth) is achieved, which is no longer inferior to the retention of mandibular advancement splints individually fabricated by a dentist.

The term "forming tray" as used before and in the following designates a "U-", arch- or horseshoe-shaped molded article that forms an open-ended shell or trough. As a rule these molded articles consist of a material that is inert and stable under physiological conditions, for example duroplastic plastics such as polytetrafluoroethylene (PTFE, Teflon®) or polycarbonates or of elastomers such as polyacrylates.

The term "fixation knob" as used above and in the following designates a rod-shaped projection with a thickened end, which are respectively attached to the side of the mandibular and/or maxillary trays, and to which the advancement mounts can be fastened reversibly. As a rule, the fixation knob is made in the shape of a tube pan, so that the terminal thickening locks into an opening in the advancement mount, thus fixes this rotatably around the longitudinal axis of the fixation knob, and simultaneously based on the preferred ball joint function, does not interfere with slight side-to-side movement of the jaws against one another.

The term "advancement mount" as used above and in the following designates a connecting element between the mandibular and maxillary trays, which makes it possible for the mandible, in the supported state, to be brought into an anterior position. It has terminal openings in which in each case a fixation knob, preferably in the form of a joint socket, can engage. The geometry of the advancement mount in and of itself is not critical; it should be long enough to bring the lower jaw into an anterior position. The rigid form of the advancement mount should be stable against elongations or compressions. On the other hand, a telescopically adjustable advancement mount should have an easily operated mechanism for adjusting the length and after adjustment is performed, should be just as stable against elongations or compressions. It must be relatively thin to guarantee good comfort in wearing. In an alternative embodiment, a telescopically adjustable advancement mount can also be designed such that it can be extended on one side, accommodating slight openings of the mouth to a certain, predetermined degree, leasing to a further increase in wearing comfort.

The statements made above and in the following regarding the geometry or the spatial arrangement of the advancement mount or parts thereof are directed toward the circumstances of the advancement mount when used as intended, i.e., after placement thereof on the upper and lower row of teeth of the individual involved: "in the longitudinal direction" means in the direction of the mouth opening ("anterior") or the throat ("posterior); "forward" (anterior) means in the direction of the mouth opening; "central" means in the area of the incisors; "back" means in the area of the rear molars; "lateral" means in the area between the premolars and the rear molars.

Advantageous embodiments of the invention are mandibular advancement splints according to the invention in which (a) the outer wall in the area between the canine teeth and the molars is interrupted; preferably the outer wall remaining in this area has a height of less than 2.0 mm, especially 1.2 to 1.8 mm, particularly preferably about 1.5 mm;

(b) the outer wall in the area of the front teeth and the fixation knob has an overall height of 4.0 to 6.0 mm, preferably of 4.5 to 5.5 mm, especially about 4.75 mm;

(c) the fixation knob has a diameter of 3.5 to 6.0 mm, preferably of 3.8 to 5.2 mm, especially about 4.4 mm (d) the outer walls of the maxillary and mandibular trays on both outsides in the area of the molars and in the area of the canine teeth, preferably at a distance of 25.0 to 35.0 mm, especially of 27.0 to 31.0 mm, particularly preferably of about 28.7 mm, measured between two fixation knobs respectively, or of about 29.8 mm measured from the respective center of the fixation knobs, in each case have a fixation head for fastening an advancement mount.

(e) the bottom of the tray in the area of the front teeth to canine teeth is partially hollow or slashed; the hollowing preferably takes place approximately over the width of the two incisors, especially over a width of 15.0 to 17.0 mm, particularly preferably of about 16.0 mm.

Based on this preferred embodiment, the arch width of the trays for the upper and lower jaws can be made narrower or wider and adjusted even more satisfactorily to the jaw shape of the respective user.

(f) the filling material (4, 5) is a toxicologically safe polymer or copolymer that can undergo plastic deformation in the presence of heat, preferably below 70° C., particularly between 40 and 65° C., and adapts closely to a predetermined shape and then retains this said shape on cooling; preferably it consists essentially of one or more copolymers of polyethylene and polyvinyl acetate or polycaprolactone. In particular the filling material has a bite channel;
(g) the molding tray consists essentially of polycarbonate;
(h) the length of the advancement mount is telescopically adjustable over a centered nut with two threads traveling in opposite directions, and at each of the two ends has an annular opening for receiving the fixation knobs;
(i) the end of the advancement mount with the annular opening is at an angle to the remainder of the advancement mount;
(j) the advancement mount can be extended via a pullout;
(k) the fixation knobs are designed as ball heads and the respective advancement mounts are fastened rotatably to them over a ball joint cup; here the diameter of the ball head at the center is advantageously 4.0 to 4.5 mm, especially 4.2 to 4.4 mm, most preferably about 4.3 mm, and on the two outer edges, 3.0 to 3.5 mm in each case, especially 3.2 to 3.4 mm, most preferably about 3.3 mm.

Also preferred in the case of the rigid advancement mounts are those made of an elastic and tear-proof material, especially of polyoxymethylene (POM, e.g., Ultraform®/BASF) or in the case of a telescopically adjustable advancement mount, their telescopic sleeves provided with the fastening elements likewise from an elastic and tear-resistant material, especially of POM, and connected together via a stainless steel connecting element.

The distance between the inside of the bottom of the maxillary tray and the inside of the bottom of the mandibular tray, in the assembled state, is preferably less than 8 mm, especially 1 to 5 mm, particularly preferably about 2 mm; this means that the distance between the teeth with the splint applied in the area of the front teeth is about 2 to 4 mm. A distance between the teeth in the front tooth area of about 2 to 3 mm with the splint applied is particularly preferred.

In this way the mouth can be closed easily and completely without muscle strain even in the case of small jaw sizes. This results in higher wearing comfort and thus also better acceptance (compliance/adherence).

An additional object of the invention is advancement mounts that are adjustable in the manner of a telescoping screw via a nut located in the center and optionally are extendable via a pull-out and at each of the two ends have an annular opening for receiving a fixation knob, wherein the one end of the advancement mount with the annular opening is angled toward the remainder of the advancement mount, characterized in that the opening has the shape of a ball cup.

Preferably the advancement mounts, the length of which is shorter than the distance between two fixation knobs, are each connected to the anterior fixation knob of the upper part and the posterior fixation knob of the lower part, wherein the mandible is brought into a more anterior position by tension; preferably wherein the molding trays each have two fixation knobs on their two outer sides at a distance of 25.0 to 35.0 mm, preferably of 27.0 to 31.0 mm, especially about 28.7 mm, and/or the advancement mounts have a total length of 25.0 to 40.0 mm, preferably 27.0 to 38.0 mm.

In an alternative embodiment the advancement mounts, the length of which is greater than the distance between two fixation knobs, are each connected to the posterior fixation knob of the upper part and the anterior fixation knob of the lower part, wherein the mandible is brought into a more anterior position by thrust; preferably wherein the molding trays each have two fixation knobs on their two outer sides at a distance of 10.0 to 20.0 mm, preferably of 12.5 to 18.0 mm, especially about 15.6 mm, and/or the advancement mounts each have a total length of 15.0 to 30.0 mm, preferably 17.0 to 27.0 mm.

The polymer or copolymer of the thermoplastic filling material can be produced separately by the injection molding process, and after slight heating of the surface thereof, pressed lightly against the insides of the two empty trays. After cooling, the two components are tightly bonded together. The polymeric composition adheres absolutely tightly to the polycarbonate composition.

If after a long wearing time of many months the adhesion of the splints to the teeth and jaws decreases, the adjustment can be performed again without problems by eating and biting down. Thus, the mandibular advancement splint can be used over a very long time period without limitations after intermittent restoration if necessary.

Embodiments of the invention are shown in the drawings and will be described in further detail in the following.

FIG. 1 shows a perspective view obliquely from the bottom and toward the front of an embodiment of the advancement splint (1) according to the invention, formed from a top part (2) and a bottom part (3), each of which is formed from a tray and a filler material (4). This filler material has a bite channel (4a). This facilitates the correct bite during fitting of the splint. The bite channel generally has a width of 7.3 to 8.5 mm, preferably 7.6 to 8.2 mm, especially about 7.8 mm in the molar area. In the front tooth area the bite channel is narrowed by about 40%, i.e., to about 5.6 mm. In addition, both the top part (2) and the bottom part (3) of the advancement splint (1) have two fixation knobs (5a, 6a, 7a, 8a; 5b, 6b, 7b, 8b) on the two side regions of each, wherein each of the two anterior fixation knobs of the lower part (5a, 5b) is connected over an advancement mount (9) to the two posterior fixation knobs (8a, 8b) of the top part.

In a preferred embodiment, the upper (2a) and lower trays (3a) (see FIG. 2) have identical shapes. About 2.0 to 4.0 cm$^3$ polycarbonate is used in producing each of them.

About 5.0 to 10.00 cm$^3$ polycaprolactone is used in producing each of the fillings of the lower and upper trays.

Figure 2:
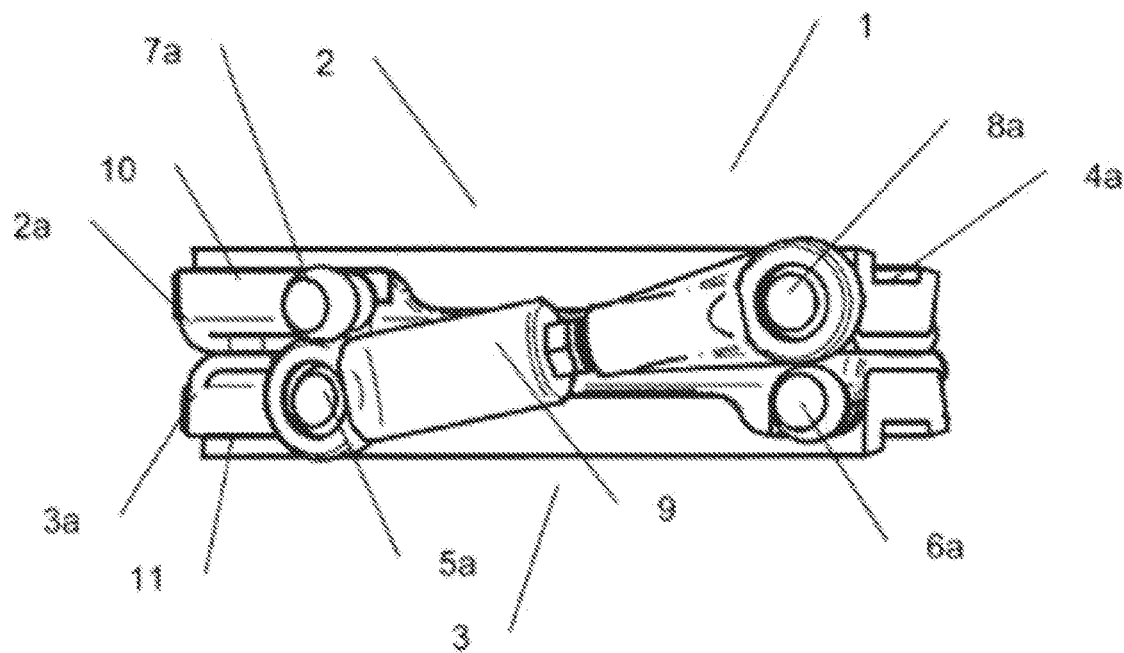
FIG. 2 shows a perspective view from the side of the same embodiment of the advancement splint according to the invention.
Figure 3:
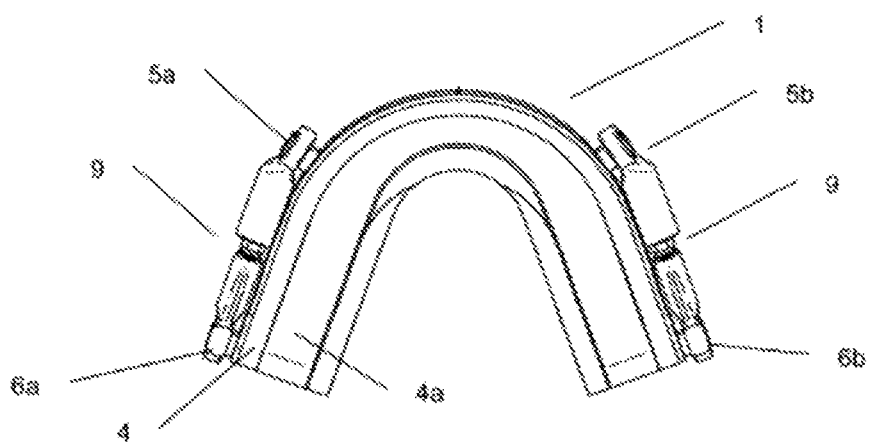
FIG. 3 shows a view from the bottom of the same embodiment of the advancement splint according to the invention.
Figure 4:
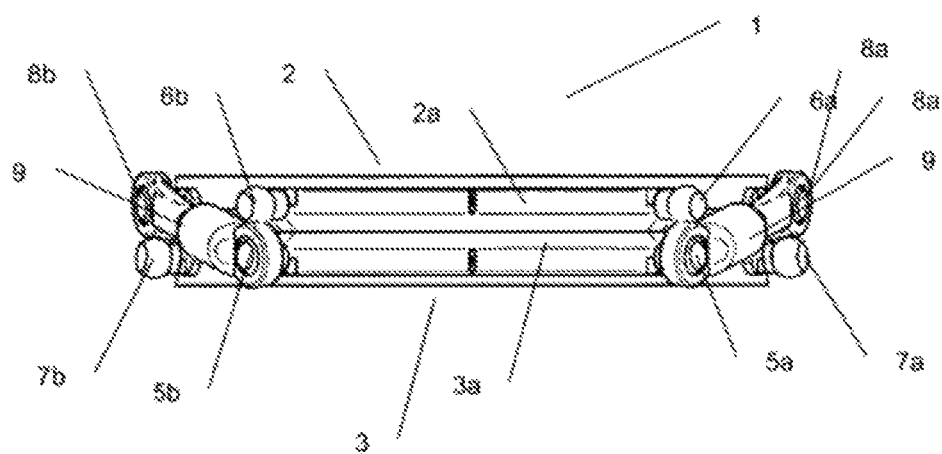
FIG. 4 shows a view from the front of the same embodiment of the advancement splint according to the invention.

FIGS. 2, 3 and 4 show perspective view of the same embodiment as FIG. 1, respectively from the side (FIG. 2), from the top (FIG. 3) and from the front (FIG. 4). This advancement splint is formed from a top part (2) and a bottom part (3), each of which is formed from a tray (2a, 3a) and a filler material (4). This filler material has a bite channel (4a). In addition, both the top part (2) and the bottom part (3) of the advancement splint (1) of FIG. 2 have two fixation knobs (5a, 6a, 7a, 8a) on the side shown of each, wherein the anterior fixation knob of the lower part (5a) is connected over an advancement mount (9) to the posterior fixation knob (8a) of the top part. This advancement mount shown is adjustable both by extension and in a telescopic manner (see FIG. 10 and FIG. 11).

Furthermore, as is recognizable from FIG. 2, the thermoplastic material (4) in each case projects beyond the height of the outer walls (10, 11) of the molding trays (2a, 3a), preferably in the area of the incisors and posterior molars, by 0.5 to 2.0 mm, especially by 1 to 1.5 mm and in the area of the anterior molars, by 1.5 to 3.5 mm, especially by 2.0 to 3.0 mm. This leads to improved enclosure of the teeth.

Figure 5:
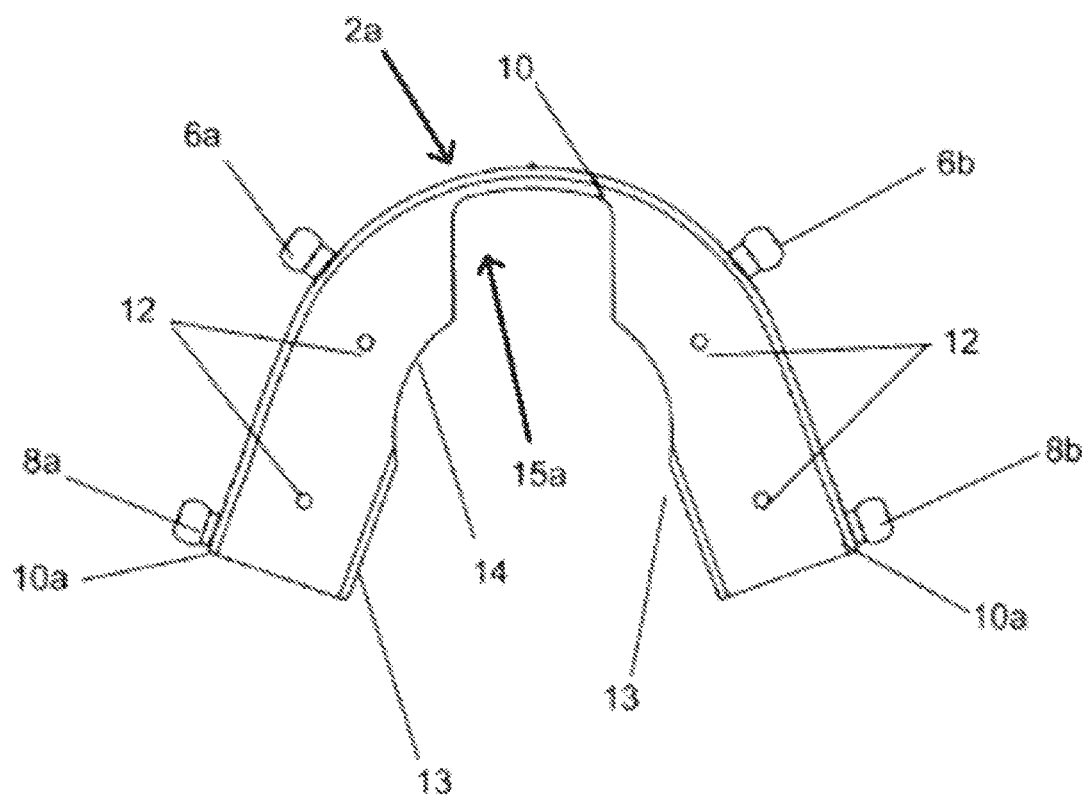
FIGS. 5 and 6 show schematic representations of an embodiment of the empty mandibular tray.
Figure 6:
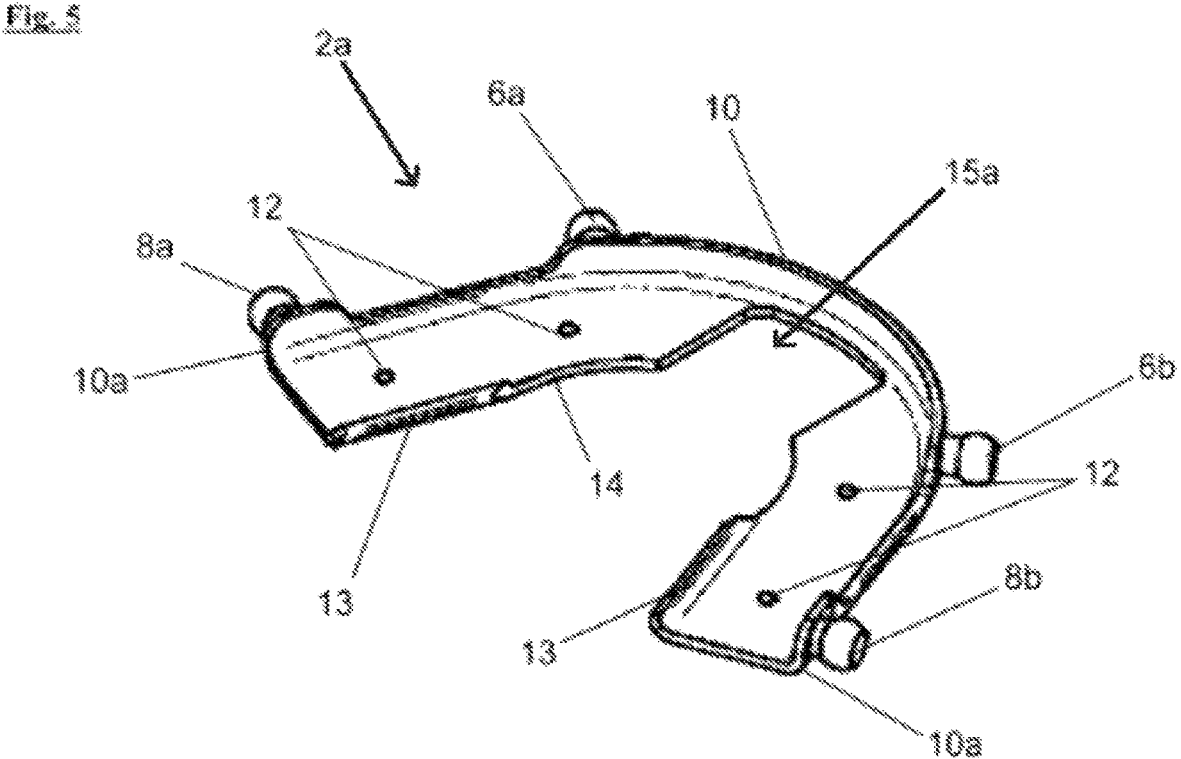

FIGS. 5 and 6 show schematic representations of an embodiment of the empty mandibular tray (2*a*) with the four fixation heads (6*a*, 8*a*, 6*b*. 8*b*). Whereas the outer wall (10) is uninterrupted between the two end points (10*a*) and only in the areas between the fixation knobs (6*a*) and (8*a*) and/or (6*b*) and (8*b*) is made distinctly lower (see FIG. 2 and FIG. 6), in the area (14) no inner wall is present, and in the posterior area the existing inner wall (13) is distinctly lower than the outer wall (10) on the opposite side. In addition, the bottom of the tray in the area of the anterior incisors (15*a*) is hollow over a width of about 16 mm and until just before the inner radius of the outer wall.

In addition, the bottoms of the respective trays have one or more, preferably 2 to 6, especially 4 essentially circular indentations or boreholes (12). These additionally increase the adhesion of the filler material to the respective tray. These indentations or boreholes (12) preferably have a diameter of 0.8 to 2.0 mm, especially of 1.2 to 1.8 mm, particularly preferably of about 1.5 mm.

The distance between the two outer walls (10*a*) at the posterior end of the upper part (maximum width of the mandibular splint) is 55 to 75 mm, preferably 60 to 72 mm, especially about 68 mm. The distance between the outer wall (10) in the area of the incisors and an imaginary line between the posterior ends of the inner wall (13) (maximum length of the mandibular splint) is 38 to 47 mm, especially about 42 mm.

Figure 7:
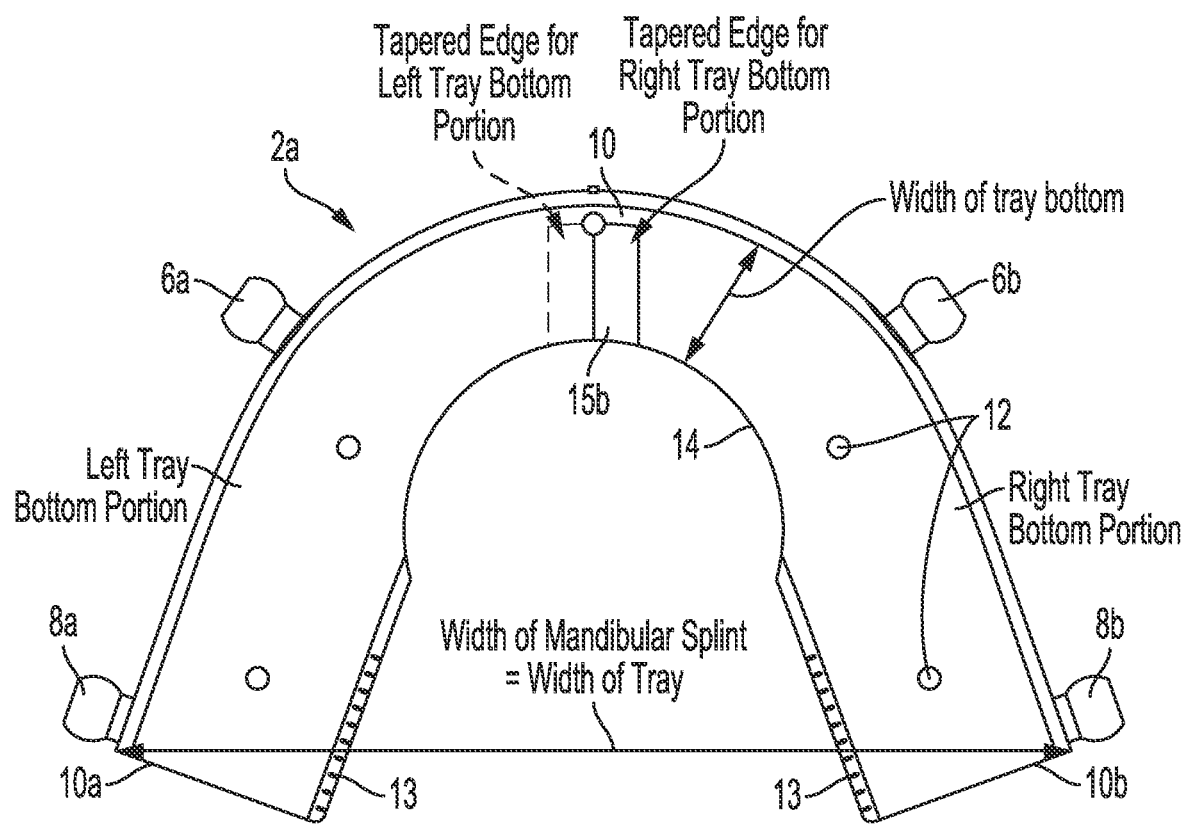
FIGS. 7 and 8 show schematic representations of an alternative embodiment of the empty mandibular tray.
Figure 8:
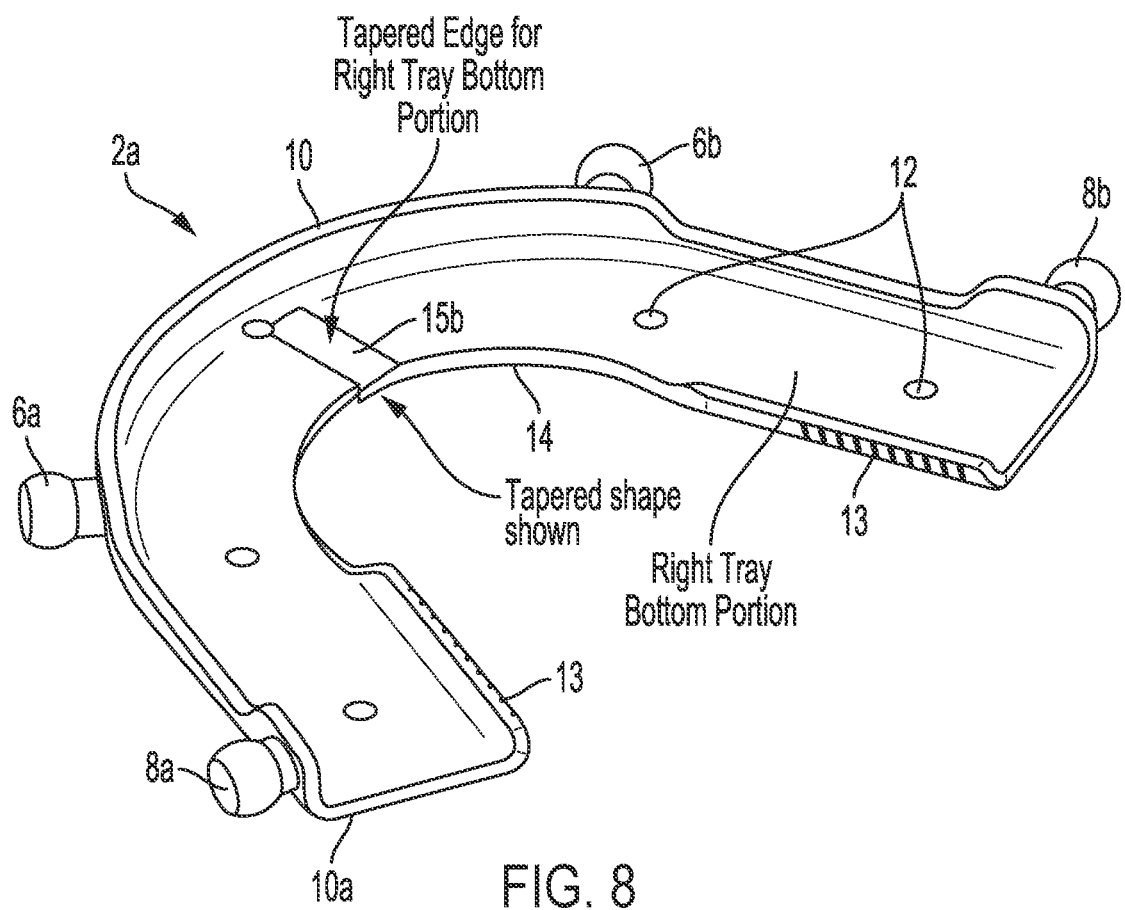

In the alternative embodiment of FIGS. 7 and 8, the tray bottom is provided with a slit (15*b*) in the area of the anterior incisor. In this case the tray bottom is preferably provided with a slit over more than 50% of its width. The length of the slit is especially 6.0 to 9.0 mm, particularly preferably about 8 mm. Preferably here the cut edges of the two halves of the splint are tapered, so that when the tray widths are narrowed the two tray bottoms can slide over one another. If the tray width is increased, the slit will widen slightly. The sliding of the bottoms of the trays over one another makes it possible to prevent the filling material from escaping the bottom of the tray.

Figure 9:
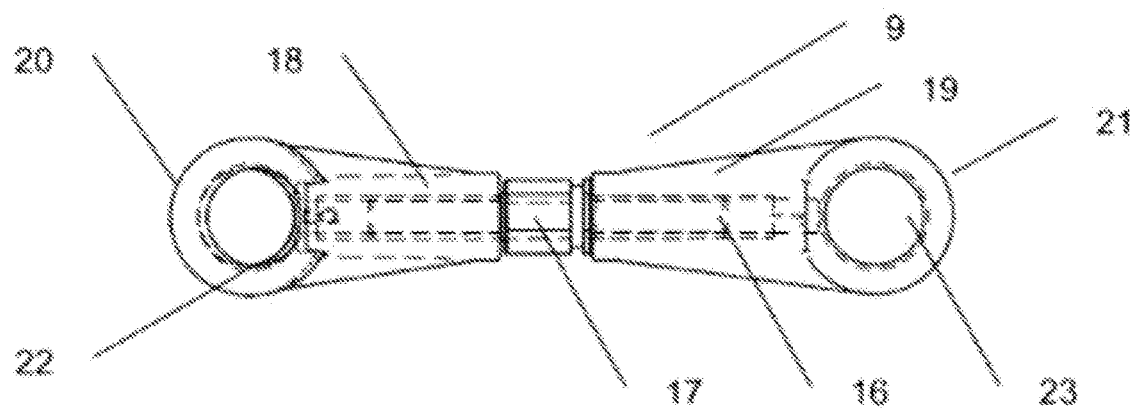
FIG. 9 shows a schematic side view of a telescopically adjustable embodiment of the advancement mount according to the invention.

FIG. 9 shows a schematic side view of a telescopically adjustable but not extendable embodiment of the advancement mount (9) with the two terminal fastening elements (20, 21) attached to the respective telescope sleeves (18, 19), completely closed on the sides, and the annular openings (22, 23) thereof. The connecting element (16) is designed as a hexagonal screw with opposing threads and can be adjusted over the hexagonal profile (17) because of the inner threads located in the telescopic sleeves, using a delicate hexagonal wrench. The diameter of the hexagonal profile is preferably about 3 mm; the diameter of the thread placed in the plastic sleeves in exemplified embodiment of FIG. 9 is about 2.9 mm.

The connecting element (16) in the non-extended state preferably has a total length of 18 to 25 mm, especially 20 to 22 mm, particularly preferably of about 21 mm. Preferably it is made of austenitic stainless steel, especially of class A2-50 or A4-50(70).

The two telescopic sleeves (18, 19) with the terminally attached fastening elements (20, 21) are made, for example, of POM and preferably have a length of 9.0 to 12.5 mm, especially 10.0 to 11.5 mm, particularly preferably about 10.9 mm, measured from the beginning of the internal thread to the center point of the respective annular opening (22, 23). The insides of the annular openings (22, 23) are curved toward the interior. In the center they have an internal diameter of preferably 4.6 to 5.0 mm, especially 4.7 to 4.9 mm, particularly preferably about 4.8 mm, and at their two edges they each have an internal diameter of preferably 4.2 to 2.6 mm, especially 4.3 to 4.5 mm, particularly preferably about 4.4 mm, and thus form ball cups for receiving the fixation heads curved toward the outside.

This telescopically adjustable advancement mount, the advancement can be achieved by pushing as shown for example in FIG. 1, but can also take place by pulling if this advancement mount is fastened to the fixation knobs (6*a*) and (7*a*) as well as (6*b*) and (7*b*) (see FIG. 4).

Figure 10:
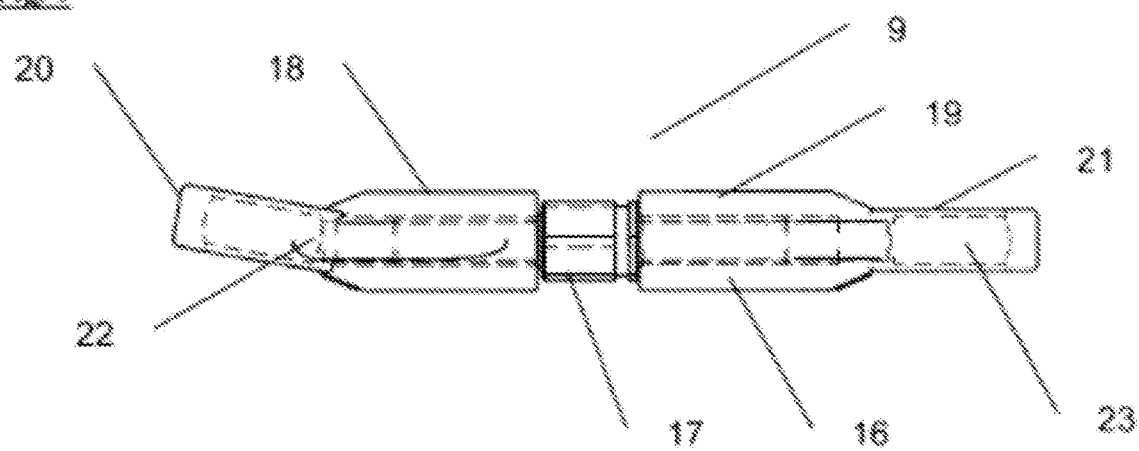
FIG. 10 shows a schematic representation of the top view of the advancement mount.

FIG. 10 shows a schematic representation of the top view of this advancement mount, the anterior fastening element (20) of which is slightly angled relative to the corresponding telescopic sleeve (18). The angle formed between (20) and (18) is less than 180° and is preferably 150 to 178°, especially 160 to 175°.

Figure 11:
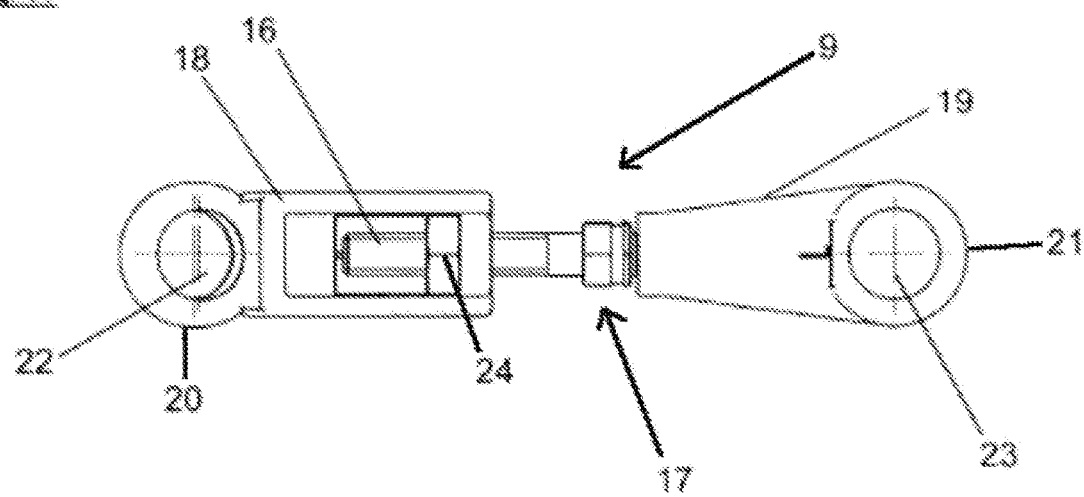
FIG. 11 shows a side view of an extendable and telescopically adjustable embodiment of the advancement mount according to the invention.
Figure 13:
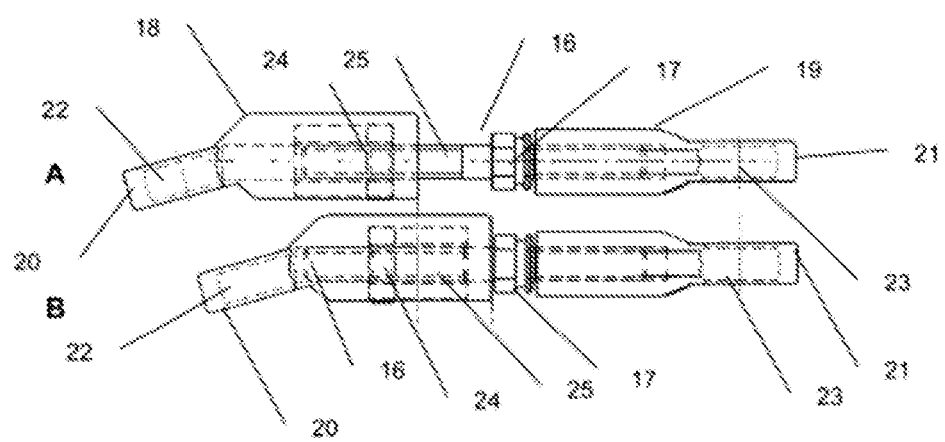

FIG. 11 shows a side view of an extensible and telescopically adjustable embodiment of the advancement mount according to the invention. Whereas the posterior telescopic sleeve (19) and the two fastening elements (20, 21) are designed in the same was as that of the advancement mount of FIG. 9, the anterior telescopic sleeve (18) is open on one side. This telescopic sleeve, in contrast to the telescopic sleeve (19), does not have an internal threading, but surrounds the outer circumference of the set screw (24), so that the connecting element (16) between the limit stop of the set screw (24) on the side of the telescopic sleeve (18) facing away from the fastening element (20) and the limit stop of the hexagonal nut (17) can be pulled out. The maximum length of this pull-out (25) can be adjusted appropriately using the hexagonal nut (17). The pull-out (25) can correspondingly be freely set using the set screw (17) between 0.0 and 10 mm, preferably between 8.0 and 1.0 mm, especially between 4.0 and 5.0 mm. The pull-out, for example, with the splint in place, moves out upon opening the mouth, wherein the set advancement of the mandible is maintained.

FIG. 12 shows a schematic representation of the top view of this advancement mount in pulled-out form (A) with a pull-out of about 4.5 mm, and in pushed-together form (B), the anterior fastening element (20) of which is slightly angled relative to the corresponding telescopic sleeve (18). The angle formed between (20) and (18) is less than 180° and is preferably 150 to 178°, especially 160 to 175°, for example about 170°. The insides of the annular openings (22, 23) are curved inwardly and thus form ball cups for receiving the fixation heads, curved toward the outside.

The distance between the two walls (11, 13) of the tray on the posterior side is preferably 14.0 to 16.0 mm, especially 14.2 to 15.6 mm, particularly preferably about 14.8 mm.

The wall thickness of the outer walls (10, 11), the inner walls (13) and the respective bases is preferably 1.0 to 2.0 mm, especially 1.2 to 1.8 mm, particularly preferably about 1.5 mm. The adaptation of the advancement splint to the jaw of the affected person is simple. The adjustment can normally be performed by any physician, regardless of specialty, their instructed staff members, or usually also by the affected person alone with the aid of a mirror.

If misaligned teeth, a history of mandibular joint problems or dental diseases such as periodontitis etc. are present, it is advisable to consult a dentist before adjusting.

When adapting the splint according to the invention, first the top part (2) is heated to a temperature above the softening point of the filling material (4), preferably in a water bath at a water temperature above 50° C., especially in a boiling water bath, is performed for about 20-30 seconds, wherein the filling material becomes plastic. Then the upper part is fitted to the dentition of the upper jaw by pressing the teeth to a uniform depth into the soft, plastic, still warm filler material. Then the filler material is allowed to cool briefly in the mouth for about 30-60 seconds, and then finally hardened completely in a cold water bath.

Then the bottom part (3) is heated correspondingly and fitted, as described above, to the teeth of the lower jaw. Then the two adapted jaw trays are connected together with 2 advancement mounts of the same length. With regard to the extendable telescopic connector (see FIGS. 11, 12) it is recommended that these always be fixed in the molar area of the maxillary tray (see FIG. 4: 8*a*, 8*b*) and fixed in the front area of the mandibular tray (see FIG. 4: 5*a*, 5*b*), i.e., the advancement of the mandible is achieved by pushing. Only if the non-extendable telescope is used (see FIGS. 9, 10) can the advancement setting be performed, depending on the mandibular advancement realizable with this, also by the opposing attachment of the telescopic connectors, thus at the top front (FIG. 4: 6*a*, 6*b*) and bottom rear (FIG. 4: 7*a*, 7*b*).

The mandibular advancement splint eliminates or reduces snoring and suspension of breathing due to obstructive sleep apnea. Due to its extremely petite size, its wearing comfort is very high. It provides solid, secure retention for the covered teeth, can be adapted continuously to the patient's needs in terms of the mandibular advancement using the telescopically movable advancement mount, and protects the teeth from nocturnal bruxism.

The invention claimed is:

1. A two-part mandibular advancement splint for preventing snoring and/or obstructive sleep apnea, comprising:
a lower and an upper part comprising an arcuate, molding tray, in each case open toward the lower and upper jaw respectively, with a base, an exterior wall and optionally an interior wall, wherein its outer walls on both outsides in the area from the molars to the canine teeth have one or more fixation knobs for fastening an advancement holder, which is fastened rotatably respectively to one fixation knob each of the lower and upper tray, and brings the mandible into a posterior or anterior position, and each of these trays contains a thermoplastic filling material that can be shaped to the teeth of the maxilla and mandible, wherein, when present, the interior wall of both trays is interrupted in the area of the front to canine teeth and each tray base is provided with a slit in the area of the anterior incisors partially separating each tray base into two tray bottom portions, wherein the cut edges of the slit are tapered toward the slit with the tapers orthogonal to the slit, so that when widths of the trays are narrowed the two tray bottom portions can slide over one another.

2. The mandibular advancement splint according to claim 1, wherein more than 50% of the width of the tray base is provided with the said slit.

3. The mandibular advancement splint according to claim 1, wherein the outer wall in the area of the front teeth and the fixation knobs has an overall height of 4.0 to 6.0 mm.

4. The mandibular advancement splint according to claim 1, wherein the outer walls of the lower and upper trays on both outer sides in the area of the molars and in the area of the canine teeth in each case have the fixation knob.

5. The mandibular advancement splint according to claim 1, wherein the lower part and the upper part are essentially identical.

6. The mandibular advancement splint according to claim 1, wherein the layer thickness of the thermoplastic filling material is 2 to 4 mm.

7. The mandibular advancement splint according to claim 1, wherein the filling material is a biocompatible, toxicologically safe polymer or copolymer, which can undergo plastic deformation under heating, and adapts closely to a predetermined shape and then retains this said shape on cooling.

8. The mandibular advancement splint according to claim 7, wherein the filling material can undergo plastic deformation below 70° C.

9. The mandibular advancement splint according to claim 8, wherein the filling material can undergo plastic deformation at a temperature between 40 and 65° C.

10. The mandibular advancement splint according to claim 1, wherein the molding tray essentially consists of a polycarbonate.

11. The mandibular advancement splint according to claim 1, wherein the length of the advancement holder is telescopically adjustable over a centered nut with two threads traveling in opposite directions, and at each of the two ends has an annular recess for receiving the fixation knobs.

12. The mandibular advancement splint according to claim 1, wherein one end of the advancement holder with the annular recess is at an angle to the remainder of the advancement holder.

13. The mandibular advancement splint according to claim 1, wherein the advancement holder can be elongated by means of a pull-out.

14. The mandibular advancement splint according to claim 1, wherein the fixation knobs are formed as ball bearing heads and the respective advancement holders are fastened rotatably therein by means of a ball bearing cup.

15. The mandibular advancement splint according to claim 14, with an advancement holder, which is telescopically adjustable by way of a hexagonal nut located in the center and optionally extendable via a pull-out and at each of the two ends has an annular opening for receiving a fixation knob located on the mandibular advancement splint, wherein the one opening has the shape of a ball bearing cup, and the one end of the advancement holder with the annular opening is angled toward the remainder of the advancement holder.

16. The mandibular advancement splint according to claim 1, wherein the slit has a uniform width along the cut edges prior to the widths of the trays being narrowed or increased.

17. The mandibular advancement splint according to claim 1, wherein the sliding of the two tray bottom portions over one another prevents the filing material from escaping the trays.

18. A ready-to-use kit for producing a mandibular advancement splint for preventing snoring and/or (obstructive) sleep apnea comprising:
(A) a lower part and an upper part, comprising an arcuate molding tray opened in each case during use toward the mandible and maxilla, with a base, an outer and optionally an inner wall, wherein its outer walls on both exterior sides in the area from the molars to the canine teeth have one or more fixation knobs for fastening a rigid, telescopically adjustable and/or extensible advancement holder, and each of these trays contains a thermoplastic filling material that can be shaped to the teeth of the maxilla and mandible, wherein, when an inner wall is present, the tray has no inner wall in the area of the front to the canine teeth and the tray base is provided with a slit in the area of the anterior incisors partially separating the tray base into two tray bottom portions, wherein the cut edges of the slit are tapered toward the slit with the tapers orthogonal to the slit, so that when a width of the tray is narrowed the two tray bottom portions can slide over one another;
(B) two or more rigid, telescopically adjustable and/or extendable advancement holders; and
(C) optionally, user instructions for using the mandibular protrusion splint.

19. The ready-to-use kit according to claim 18, wherein the lower part and the upper part are essentially identical.

20. The ready-to-use kit according to claim 18, wherein:
the slit has a uniform width along the cut edges prior to the widths of the trays being narrowed or increased; and
the sliding of the two tray bottom portions over one another prevents the filing material from escaping the trays.

* * * * *